United States Patent [19]
Wolfe et al.

[11] Patent Number: 5,348,025
[45] Date of Patent: Sep. 20, 1994

[54] APPARATUS AND METHOD FOR MEASURING MOBILITY OF THE SCAPHOID

[75] Inventors: Scott W. Wolfe, Fairfield; Joseph J. Crisco, Cheshire, both of Conn.

[73] Assignee: Yale University, New Haven, Conn.

[21] Appl. No.: 20,773

[22] Filed: Feb. 22, 1993

[51] Int. Cl.$^5$ ............................................. A61B 5/103
[52] U.S. Cl. .................................................. 128/782
[58] Field of Search ............... 128/739, 740, 744, 774, 128/782

[56] References Cited

U.S. PATENT DOCUMENTS

| | | | |
|---|---|---|---|
| 3,133,355 | 5/1964 | Gordon | 128/782 |
| 4,180,059 | 12/1979 | Tiep | 128/782 |
| 4,236,528 | 12/1980 | Stanec et al. | 128/782 |
| 4,549,555 | 10/1985 | Fraser et al. | 128/782 |
| 4,571,834 | 2/1986 | Fraser et al. | 128/782 |
| 4,583,555 | 4/1986 | Malcom et al. | 128/782 |
| 4,649,934 | 3/1987 | Fraser et al. | 128/782 |
| 4,913,163 | 4/1990 | Roger et al. | 128/782 |
| 5,156,163 | 10/1992 | Watkins et al. | 128/782 |

OTHER PUBLICATIONS

Measure Knee Stability, MEDmetric Corporation, San Diego, California, 1990—product brochure.
Document Knee Stability, MEDmetric Corporation, San Diego, California, 1990—product brochure.
Daniel, Dale M., "The Accuracy and Reproducibility of the KT1000 Knee Ligament Arthrometer", Courtesy of MEDmetric Corporation, San Diego, California, 1990.
High Speed Tibio–Femoral Gait Passive Pivot Shift, Faro Knee–KG Computerized Knee Kinetogram, Faro Medical Technologies, Inc., San Diego, California, 1988—product brochure.
Genucom Product Literature describing patello femoral option etc., 1986—product brochure.
MEDmetric Measurement News—product brochure, 1989.
Knee Laxity Tester, Orthopedic Systems, Inc. Hayward, Calif.—product brochure Jan. 1993.
Genucom, Faro Medical Tech., Inc.—product brochure Jan. 1983.
Knee Analysis Systems, Faro Genucom, Faro Medical Tech, Inc.—product brochure Jan. 1993.

Primary Examiner—Max Hindenburg
Attorney, Agent, or Firm—Fish & Richardson

[57] ABSTRACT

An apparatus and method for measuring mobility of a subject's scaphoid. The apparatus includes a force applicator that applies a variable force to the scaphoid, a load cell that generates a first signal corresponding to the magnitude of the force, and a displacement sensor that generates a second signal corresponding to a displacement of the scaphoid in response to the applied variable force.

21 Claims, 4 Drawing Sheets

APPARATUS AND METHOD FOR MEASURING MOBILITY OF THE SCAPHOID

BACKGROUND OF THE INVENTION

In wrist trauma cases, injury commonly occurs to the ligaments stabilizing the scaphoid 10, a bone located near the thumb. (See FIG. 1.) When injury occurs, the ligaments are stretched or torn, thereby increasing the mobility of the scaphoid 10 with respect to the other carpal bones. Thus, injury to the ligaments can be detected by measuring the displacement of the scaphoid 10 in response to an applied force.

In recognition that injury to the ligaments can be detected in this manner, Watson developed a "scaphoid" test. See Watson, H. K., in *Operative Hand Surgery*, 2nd ed. Green, D. P., editor. Churchill Livingston, New York, 1988, p. 143. A clinician performs the scaphoid test by placing his four fingers on the back of the subject's radius and his thumb on the scaphoid 10. (See FIG. 2.) The right hand is used to examine the right wrist and vice versa. While moving the subject's hand from side to side, the clinician holds the scaphoid 10 in place with his thumb and applies a force to rotate the scaphoid 10 and drive the proximal pole of the scaphoid 10 dorsally. Excessive movement may indicate ligamentous injury. Once thoroughly familiar with the test, the clinician can readily detect excessive movement of the scaphoid 10.

The Watson "scaphoid" test, however, is extremely subjective and difficult to replicate. Because the test is performed strictly by sense of touch, results of the examination are inconsistent from one subject to the next and are highly operator dependent.

SUMMARY OF THE INVENTION

In general, in one aspect, the invention is an apparatus for measuring mobility of a subject's scaphoid. The apparatus includes a force applicator that applies a variable force to the subject's scaphoid, a load cell that generates a first signal corresponding to the magnitude of the applied variable force, and a displacement sensor that generates a second signal corresponding to a displacement of the scaphoid in response to the applied variable force.

In preferred embodiments, the force applicator is a plunger assembly by which a user can manually apply a force to the subject's scaphoid. The plunger assembly includes a handle, a rod and a bearing assembly guiding the rod. In that plunger assembly, the load cell is located between the handle and the rod. In addition, the force applicator includes an end piece having a concave region which contacts the subject's hand. The end piece is a cap fitting over the end of said rod.

Also in preferred embodiments, the load cell includes a plurality of strain gauges mounted on a hollow ring. For example, it might include four strain gauges which are connected to form a Wheatstone bridge. Furthermore, the displacement sensor includes a linear voltage displacement transducer and there is a rigid member coupling that transducer to the plunger assembly. The apparatus also includes a display device (e.g. a monitor including video screen) displaying the second signal as a function of the first signal for a range of forces applied to the subject's scaphoid. The apparatus further includes a support structure for supporting the subject's hand in a position so as to perform scaphoid mobility measurements. The support structure includes an arm rest having an arm restraint (e.g. velcro straps) for securing the subject's forearm to the arm rest. The support structure also includes a hand support for supporting the subject's hand. The hand support includes a restraint (e.g. also velcro straps) securing the subject's hand to the hand support.

In general, in another aspect, the invention is a method for measuring mobility of a subject's scaphoid. The method includes the steps of applying a variable force to the scaphoid, measuring the variable force, measuring the displacement of the scaphoid in response to the force, and displaying the displacement of the scaphoid versus the measured variable force.

The invention provides a reproducible objective test for measuring the mobility of the scaphoid and thereby detecting ligament injury.

DESCRIPTION OF THE PREFERRED EMBODIMENT(S)

Figure 1:
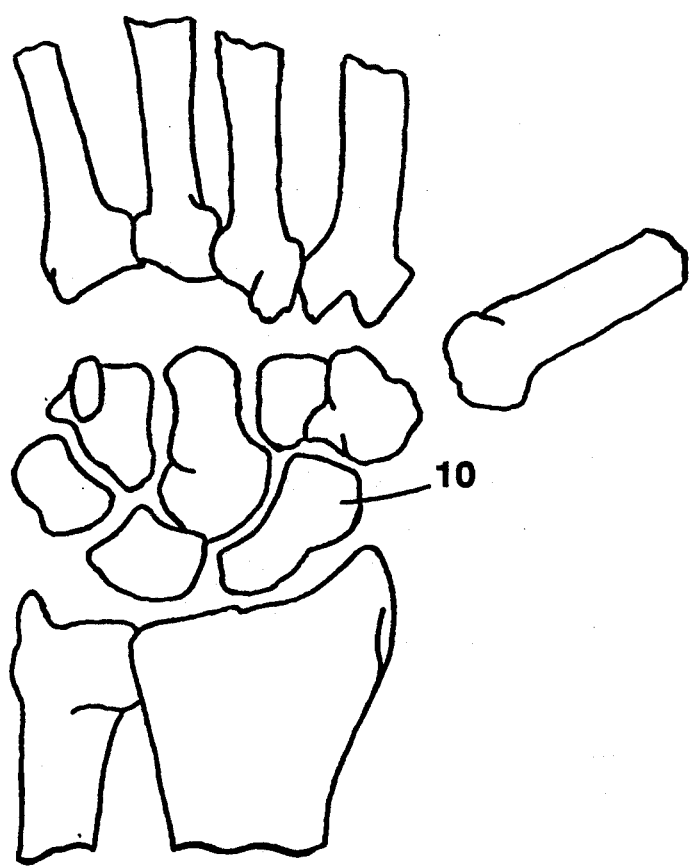
FIG. 1 (prior art) shows the skeletal structure of a human right hand.
Figure 2:
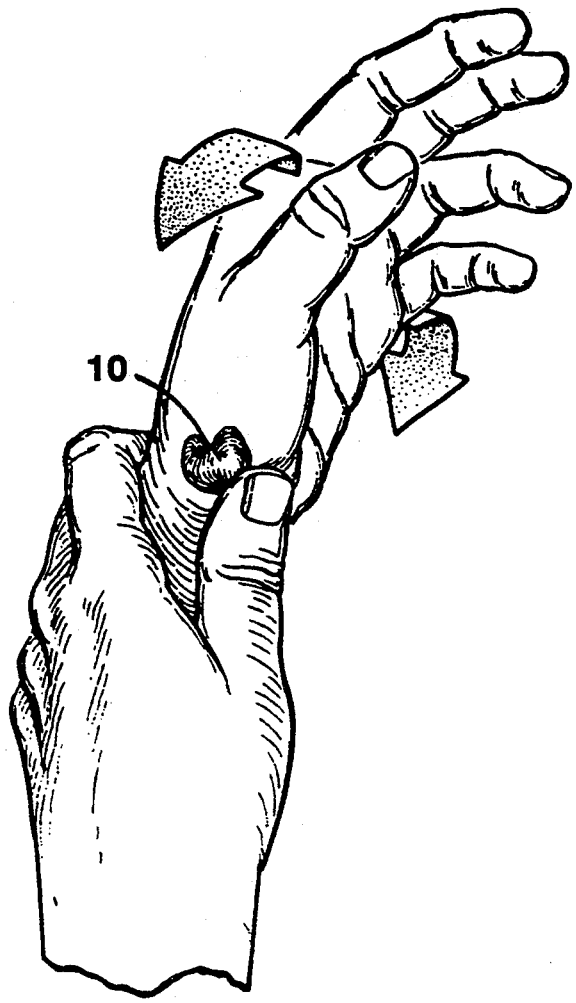
FIG. 2 (prior art) illustrates the Watson "scaphoid" test.
Figure 3:
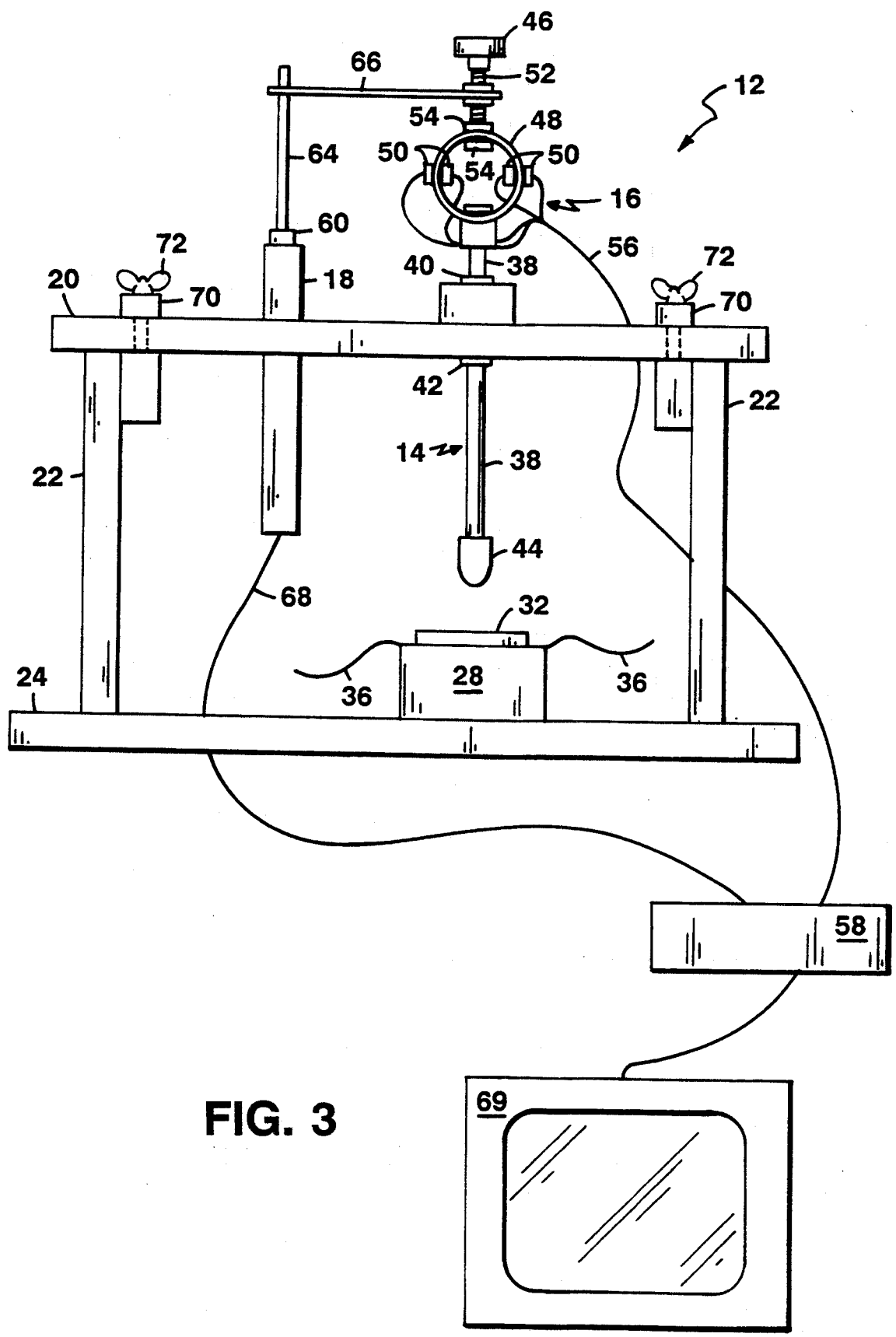
FIG. 3 shows a scaphometer.
Figure 4:
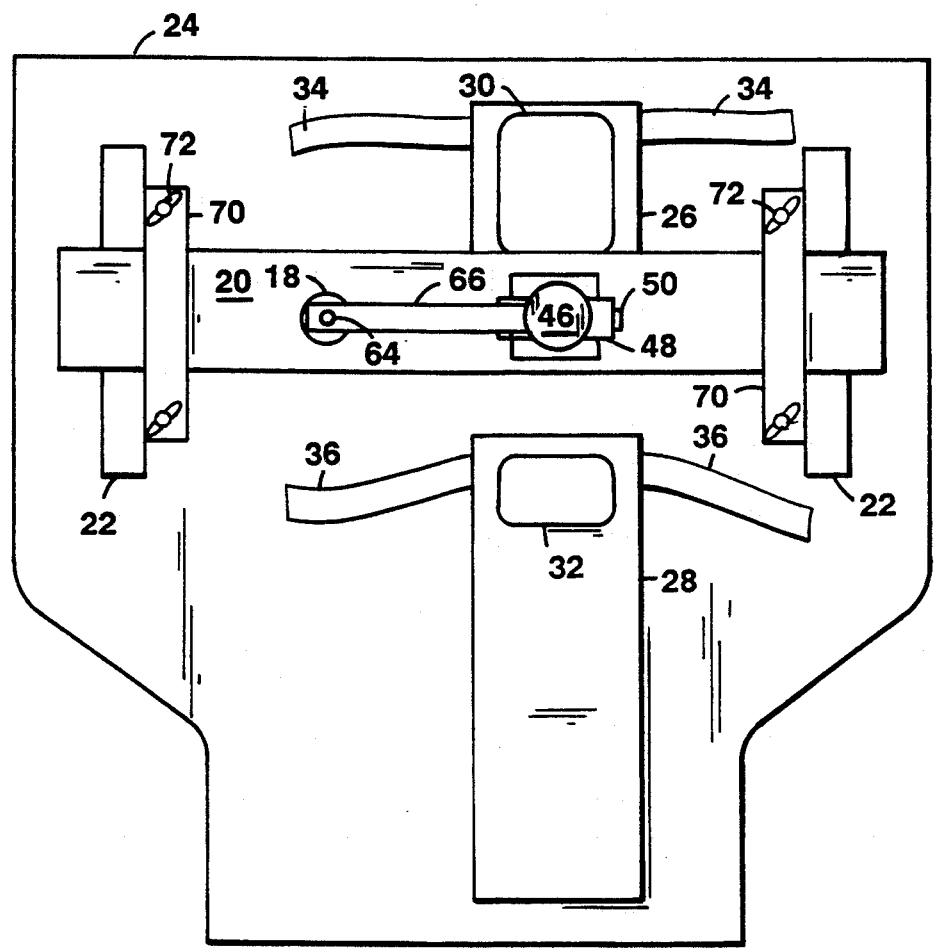
FIG. 4 is a top view of the scaphometer of FIG. 3.

Referring to FIGS. 3–4, the described embodiment of the invention is a device (referred to herein as a scaphometer 12) for measuring the mobility of a subject's scaphoid 10 (FIGS. 1, 2). Scaphometer 12 includes a plunger assembly 14 for applying a variable force to a subject's scaphoid 10, a load cell 16 for measuring the amount of force that is being applied by plunger assembly 14 to the scaphoid, and a displacement sensor 18 for measuring the amount by which the scaphoid 10 moves in response to the applied force. These three devices are mounted on a cross member 20 which rests on two base supports 22 that are attached to a platform 24. Between base supports 22 and resting on platform 24, there is a horizontal structure for holding the subject's supinated hand during the measurements of scaphoid mobility. The horizontal structure includes a hand support platform 26 and an arm support platform 28. On platforms 26 and 28 there are pads 30 and 32 which serve to support the subject's hand in a horizontal orientation. Attached to support platforms 26 and 28 are velcro straps 34 and 36 for strapping the subject's wrist and fingers securely in place so as to minimize any undesired movement that might introduce errors into the measurements.

Plunger assembly 14 includes a steel rod 38 passing through a pair of linear bearings 40 and 42 that guide the free vertical travel of steel rod 38 and prevent its lateral movement. Covering the lower end of steel rod 38 is a plastic or rubber tip 44 which is dimpled to accept the scaphoid tubercle and thereby produce a more stable transfer of force from the plunger assembly to the subjects scaphoid (see FIG. 5 which shows the dimple is cross-sectional view of the end of steel rod 38). At the upper end of steel rod 38 is load cell 16 to which is attached a handle 46 that allows the examiner to apply a dorsally directed load to the subject's scaphoid. Handle 46 is attached to load cell 16 by a threaded bolt 52 and nuts 54.

In the described embodiment, load cell 16 is a strain gauge cell constructed from a steel ring 48 and four strain gauges 50. Steel rod 38 is attached to one side of ring 48 (for reference identified as 0° on the ring) and threaded bolt 52 with handle 46 is attached to ring 48 at 180° from the 0° reference point, i.e., on the opposite side of ring 48 from where threaded rod 52 is attached). At locations on ring 48 corresponding to 90° and 270° the four strain gauges are affixed to ring 48, two gauges at each location, one gauge on the inside of ring 48 and the other gauge on the outside of ring 48. Strain gauges 50, which are thin wire resistors, have leads 56 that are connected to a data acquisition module 58. In data acquisition module 58 strain gauges are connected to form a Wheatstone bridge. When the examiner exerts a force on handle 46, this force is transferred down through ring 48, causing it to deform. The deformation of ring 48 changes the resistances of strain gauges 50 to change relative to each other thereby causing the Wheatstone bridge to become unbalanced. The bridge, in turn, generates a signal which is a measure of the amount of force that the examiner has applied to the subject's scaphoid.

Displacement sensor 18 is a linear voltage displacement transducer (LVTD) including a magnetic core 60 that is free to slide up and down in displacement sensor 18. The movement of the magnetic field generated by core 60 serves to change a voltage appearing across leads 62 of displacement sensor 18. In the described embodiment, displacement sensor 18 is a 1000 HR-DC available commercially from Schaevitz in Pennsauken, N.J.

The vertical movement of rod 38 in plunger assembly 14 is transferred to core 60 via a rigid aluminum plate 66 that is in turn connected to an aluminum tube 64 affixed to the top of core 60. Aluminum plate 40 is attached to plunger assembly at threaded bolt 25 using two steel nuts. This direct connection causes magnetic core 60 to move in unison with rod 38, which ensures that a displacement measured by a change in the voltage of displacement sensor 14 at leads 68 will directly correspond to a force measured by a change in the voltage of load cell 16 at leads 56. Because the voltage-displacement relationship is linear, the change in the voltage output can be used to determine the core displacement, which is equal to the displacement of the scaphoid 10.

Leads 68 from displacement sensor 18 are connected to data acquisition unit 58 which displays the displacement as a function of applied force on a display device 69, e.g. a computer display screen or a pen plotter. Acquisition unit 58 also includes memory in which all of the data points can be stored for future processing and analysis.

Cross member 20 is connected to base supports 22 by braces 70 and wing nuts 72. When wing nuts 72 are loosened, the examiner can reposition rod 38 of plunger assembly 14 to align with the subject's scaphoid. Tightening the wing nuts after proper alignment, then stabilizes support 20 and prevent its lateral movement during the measurements.

Having set forth the structure of the preferred embodiment, its operation will now be described.

Figure 5:
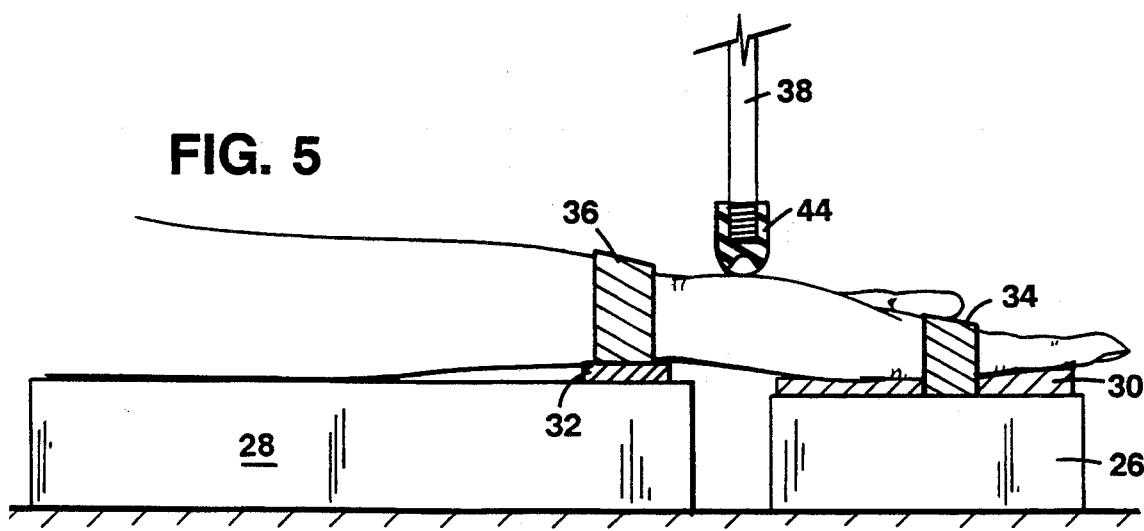
FIG. 5 illustrates a subject's arm positioned in the scaphometer.

Referring to FIG. 5, an examiner places the subject's forearm, with the palm facing upward, on arm support platform 28. The arm is positioned so that the backs of the subject' fingers and the portion of the hand including the metacarpals rest on hand support platform 26. The back of the subject's hand below the scaphoid is unsupported by either support 28 or support 26. It is important that the back of the hand in the vicinity of the scaphoid not be directly supported because, if it were, a palmarly applied force to the scaphoid 10 would cause a corresponding dorsal reaction force, and these two forces would compress the carpal arch, thus changing the behavior of the scaphoid 10. After proper positioning, the examiner using straps 22 and 23 straps the subject's hand and forearm in place, thereby constraining movement of the radius/ulna and further reducing the likelihood of erroneous data.

After securing the subject's fingers and forearm, the examiner adjusts the scaphometer 12 so that rubber tip 44 is resting on the subject's hand above at the location of the scaphoid. Once the rubber tip 44 is properly positioned and support 20 is secured in place, the examiner applies a variable force to the subject's scaphoid by pushing down on handle 46. The resulting displacement and force signals are displayed on display device 68. By varying the amount of force applied, the examiner can obtain a plot of load vs. displacement.

In the described embodiment, the data acquisition module is a personal computer which samples the analog signals from the load cell and the displacement sensor. The computer is programmed to audibly alert the examiner when the load reaches a maximum load beyond which there may be discomfort to the subject (e.g. about 40 Newtons). To determine the slope of the resulting curve (i.e., the stiffness in N/mm) a commercially available software program (e.g. MATHPAK 87, Precision Plus Software, Ontario, Canada) is used to compute a linear least squares fit to the data points.

Figure 6:
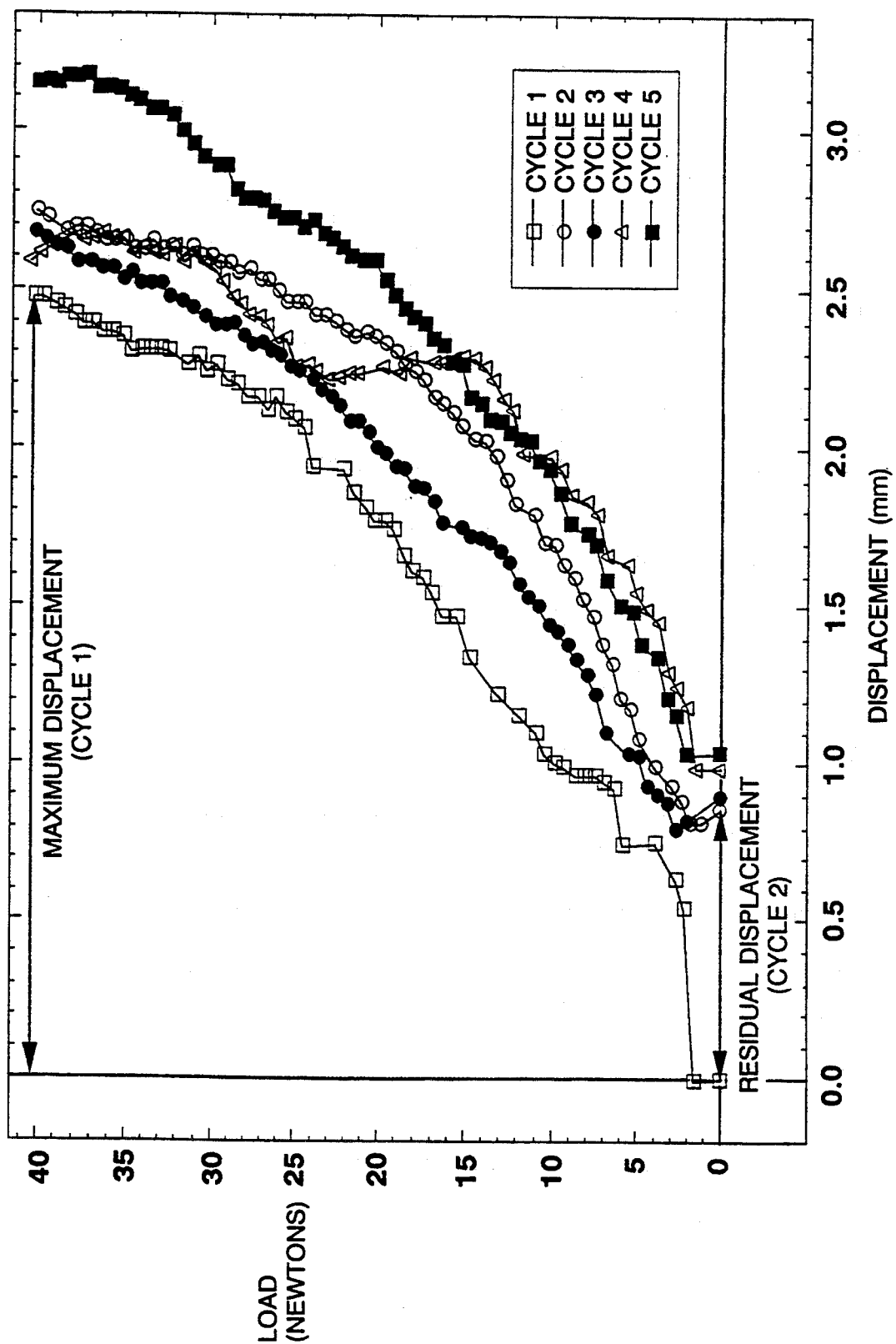
FIG. 6 presents mobility measurements made with the scaphometer.

Typical results for a single test of 5 cycles of a healthy subject (i.e., no injury to the scaphoid ligaments) are presented as load-displacement curves in FIG. 6. The vertical axis is load measured in newtons and the horizontal axis is displacement measured in millimeters. Each curve demonstrates an approximately linear behavior, with a trend toward increased stiffness with increasing load. Note that with each successive loading cycle, the curves tended to shift along the displacement axis as residual and maximum displacement increased, while stiffness was unchanged. It has been observed from these tests that load-displacement behavior was repeatable with either sufficient preconditioning or with sufficient rests between tests.

Other embodiments are within the following claims. For example, a number of alternative devices could be used to hold the subject's hand in position for conducting the measurements. The hand support could be a cradle contoured to accept the subject's hand, it could include an inflatable glove which upon inflation firmly grasps and thereby stabilizes the subject's hand, or it could be a vise-like structure including a locking device for holding the hand.

What is claimed is:

1. Apparatus for measuring mobility of a free-floating bone in a subject's wrist, said apparatus comprising:
   a support structure designed to support the subject's hand and to permit unobstructed movement of the free-floating bone when supporting the subject's hand,
   a force applicator positioned over and applying a variable force to said free-floating bone while the subject's hand is being supported by the support structure, a load cell generating a first signal corresponding to the magnitude of said variable force, and a displacement sensor generating a second signal corresponding to a displacement of said free-floating bone in response to said variable force.

2. The apparatus of claim 1 wherein said free-floating wrist bone is the scaphoid.

3. The apparatus of claim 2 wherein said force applicator comprises a plunger assembly by which a user can manually apply a force to the subject's scaphoid.

4. The apparatus of claim 3 wherein said plunger assembly comprises a handle, a rod and a bearing assembly guiding said rod.

5. The apparatus of claim 4 wherein said load cell is located between said handle and said rod.

6. The apparatus of claim 1 wherein said force applicator includes an end piece having a concave region which contacts the subject's hand.

7. The apparatus of claim 6 wherein said end piece is a cap fitting over the end of said rod.

8. The apparatus of claim 1 wherein said force applicator comprises a plunger assembly by which a user can manually apply a force to the subject's scaphoid and wherein said apparatus further comprises a rigid member coupling said displacement sensor to the plunger assembly.

9. The apparatus of claim 2 further comprising a display device displaying said second signal as a function of said first signal for a range of forces applied to the subject's scaphoid.

10. The apparatus of claim 11 wherein said display device comprises a video screen.

11. The apparatus of claim 2 further comprising a support structure for supporting the subject's hand in a position so as to perform scaphoid mobility measurements.

12. The apparatus of claim 11 wherein said support structure comprises an arm rest.

13. The apparatus of claim 12 wherein said arm rest includes an arm restraint for securing the subject's forearm to the arm rest.

14. The apparatus of claim 13 wherein said arm restraint comprises velcro straps.

15. The apparatus of claim 11 wherein said support structure further comprises a hand support for supporting the subject's hand.

16. The apparatus of claim 15 wherein said hand support further comprises a restraint securing the subject's hand to the hand support.

17. The apparatus of claim 16 wherein said hand restraint comprises velcro straps.

18. Method for measuring mobility of a free-floating bone in a subject's wrist, said method comprising the steps of:

applying a variable force to said free-floating bone, measuring said variable force, measuring displacements of said free-floating bone in response to said force, and displaying the displacement of said free-floating bone versus the measured variable force.

19. The method of claim 18 wherein said free-floating wrist bone is the scaphoid.

20. The method of claim 19 further comprising supporting the subject's hand during the step of applying the variable force to said free-floating bone, wherein the step of supporting the subject's hand is done in such a manner that movement of the free-floating bone is unobstructed.

21. The method of claim 20 wherein the step of supporting the subject's hand further comprises restraining the subject's hand during the force applying step.

* * * * *